United States Patent
Cong et al.

(10) Patent No.: US 9,724,521 B2
(45) Date of Patent: Aug. 8, 2017

(54) FREQUENCY BASED THERAPY GENERATION

(71) Applicant: Medtronic, Inc., Minneapolis, MN (US)

(72) Inventors: Peng Cong, Cupertino, CA (US); Timothy J. Denison, Minneapolis, MN (US); Gabriela C. Molnar, Fridley, MN (US); Forrest C. M. Pape, New Brighton, MN (US); Scott R. Stanslaski, Shoreview, MN (US); Wesley A. Santa, Andover, MN (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 14/682,855

(22) Filed: Apr. 9, 2015

(65) Prior Publication Data

US 2016/0296759 A1    Oct. 13, 2016

(51) Int. Cl.
*A61N 1/36* (2006.01)
*A61N 1/372* (2006.01)

(52) U.S. Cl.
CPC ......... *A61N 1/372* (2013.01); *A61N 1/36171* (2013.01); *A61N 1/37252* (2013.01)

(58) Field of Classification Search
CPC ............ A61N 1/36135; A61N 1/36167; A61N 1/36171
See application file for complete search history.

(56) References Cited

U.S. PATENT DOCUMENTS

| 5,983,141 A | 11/1999 | Sluijter et al. |
| 2001/0007949 A1 | 7/2001 | Silverstone |
| 2002/0177882 A1 | 11/2002 | DiLorenzo |
| 2003/0135248 A1 | 7/2003 | Stypulkowski |
| 2004/0111127 A1 | 6/2004 | Gliner et al. |
| 2006/0015153 A1 | 1/2006 | Gliner et al. |
| 2006/0173509 A1 | 8/2006 | Lee et al. |
| 2006/0293720 A1* | 12/2006 | DiLorenzo ......... A61N 1/36082 607/42 |
| 2007/0021801 A1 | 1/2007 | Heruth et al. |

(Continued)

FOREIGN PATENT DOCUMENTS

WO    2010058178 A1    5/2010

OTHER PUBLICATIONS

Albert, et al., "Deep brain stimulation, vagal nerve stimulation and transcranial stimulation: An overview of stimulation parameters and neurotransmitter release," Neuroscience and Biobehavior Reviews, Apr. 2009, pp. 1042-1060.

*Primary Examiner* — Eric D. Bertram
(74) *Attorney, Agent, or Firm* — Shumaker & Sieffert, P.A.

(57) ABSTRACT

In some examples, one or more processors determine characteristics of frequency components of a sensed bioelectrical signal. In response to determining the characteristics, the one or more processors determine therapy parameters for frequency components of a stimulation signal. The one or more processors may determine the therapy parameters based on the characteristics of the frequency components of the sensed bioelectrical signal. As another example, the one or more processors may determine the therapy parameters based on received information after the characteristics of the frequency components of the sensed bioelectrical signal are displayed to a user.

28 Claims, 6 Drawing Sheets

(56) References Cited

U.S. PATENT DOCUMENTS

| | | |
|---|---|---|
| 2007/0213783 A1 | 9/2007 | Pless |
| 2008/0103547 A1 | 5/2008 | Okun et al. |
| 2008/0269836 A1 | 10/2008 | Foffani et al. |
| 2009/0082691 A1 | 3/2009 | Denison et al. |
| 2011/0009921 A1 | 1/2011 | Tass et al. |
| 2011/0071589 A1 | 3/2011 | Starkebaum et al. |
| 2011/0144521 A1 | 6/2011 | Molnar et al. |
| 2011/0184486 A1 | 7/2011 | De Ridder |
| 2016/0175594 A1* | 6/2016 | Min ............... A61N 1/3615 607/62 |

\* cited by examiner

FREQUENCY BASED THERAPY GENERATION

TECHNICAL FIELD

The disclosure relates to therapy generation.

BACKGROUND

Medical devices, such as electrical stimulators or therapeutic agent delivery devices, may be used in different therapeutic applications, such as deep brain stimulation (DBS), spinal cord stimulation (SCS), pelvic stimulation, gastric stimulation, peripheral nerve stimulation, functional electrical stimulation or delivery of pharmaceutical agents, insulin, pain relieving agents or anti-inflammatory agents to a target tissue site within a patient. A medical device may be configured to deliver therapy to a patient to treat a variety of symptoms or patient conditions such as chronic pain, tremor, Parkinson's disease, other types of movement disorders, seizure disorders (e.g., epilepsy), urinary or fecal incontinence, sexual dysfunction, obesity, mood disorders, gastroparesis or diabetes. In some therapy systems, an electrical stimulator, which may be implantable in some instances, delivers electrical therapy to a target tissue site within a patient with the aid of one or more electrodes, which may be deployed by medical leads, on a housing of the electrical stimulator, or both. In addition to or instead of electrical stimulation therapy, a medical device, which may be implantable in some instances, may deliver a therapeutic agent to a target tissue site within a patient with the aid of one or more fluid delivery elements, such as a pump, a catheter and/or a therapeutic agent eluting patch.

SUMMARY

The disclosure describes example systems, devices, and methods for determining therapy parameters for two or more stimulation frequency components of a stimulation signal delivered by a medical device. In some examples, a medical device or a programmer for the medical device receives information representative of a bioelectrical signal, and determines one or more characteristics of sensed frequency components of the bioelectrical signal. For instance, the bioelectrical signal may be considered as a combination of a plurality of bioelectrical signals at different frequencies that together form the signal. The medical device or programmer may determine characteristics such as amplitude and/or phase of the sensed frequency components.

The medical device or programmer may determine therapy parameters for a plurality of stimulation frequency components in response to determining the characteristics of the sensed frequency components. For instance, the medical device or programmer may determine amplitude and/or phase of the stimulation frequency components. As another example, the programmer may output information indicative of characteristics of the sensed frequency components, and in response to outputting such information, receive information (e.g., from a user) indicative of the therapy parameters for the stimulation frequency components (i.e., determine the therapy parameters based on the received information indicative of the therapy parameters). In this manner, the medical device or programmer may determine therapy parameters in the frequency domain, rather than a time domain. Because bioelectrical signals include multiple frequency components, determining therapy parameters in the frequency domain may result in more efficacious treatment as compared to therapy parameters determined in the time domain.

In one example, the disclosure describes a method receiving, with one or more processors, information representative of a bioelectrical signal of a patient, determining, with the one or more processors, one or more characteristics of two or more sensed frequency components of a plurality of sensed frequency components, wherein the plurality of sensed frequency components together forms the bioelectrical signal, determining, with the one or more processors, therapy parameters for two or more stimulation frequency components of a plurality of stimulation frequency components of a stimulation signal in response to determining the characteristics of the two or more sensed frequency components, and causing, with the one or more processors, a stimulation generator to deliver the stimulation signal.

In one example, the disclosure describes a device comprising a processor and a memory. The processor is configured to receive information representative of a bioelectrical signal of a patient, determine one or more characteristics of two or more sensed frequency components of a plurality of sensed frequency components, wherein the plurality of sensed frequency components together forms the bioelectrical signal, determine therapy parameters for two or more stimulation frequency components of a plurality of stimulation frequency components of a stimulation signal in response to determining the one or more characteristics of the two or more sensed frequency components, and cause a stimulation generator to deliver the stimulation signal. The memory is configured to store the determined therapy parameters.

In one example, the disclosure describes a computer-readable storage medium having instructions stored thereon that when executed cause one or more processors to receive information representative of a bioelectrical signal of a patient, determine one or more characteristics of two or more sensed frequency components of a plurality of sensed frequency components, wherein the plurality of sensed frequency components together forms the bioelectrical signal, determine therapy parameters for two or more stimulation frequency components of a plurality of stimulation frequency components of a stimulation signal in response to determining the one or more characteristics of the two or more sensed frequency components, and cause a stimulation generator to deliver the stimulation signal.

In one example, the disclosure describes a device comprising means for receiving information representative of a bioelectrical signal of a patient, means for determining one or more characteristics of two or more sensed frequency components of a plurality of sensed frequency components, wherein the plurality of sensed frequency components together forms the bioelectrical signal, means for determining therapy parameters for two or more stimulation frequency components of a plurality of stimulation frequency components of a stimulation signal in response to determining the one or more characteristics of the two or more sensed frequency components, and means for causing a stimulation generator to deliver the stimulation signal.

The details of one or more examples are set forth in the accompanying drawings and the description below. Other features, objects, and advantages will be apparent from the description and drawings, and from the claims.

DETAILED DESCRIPTION

Figure 1:
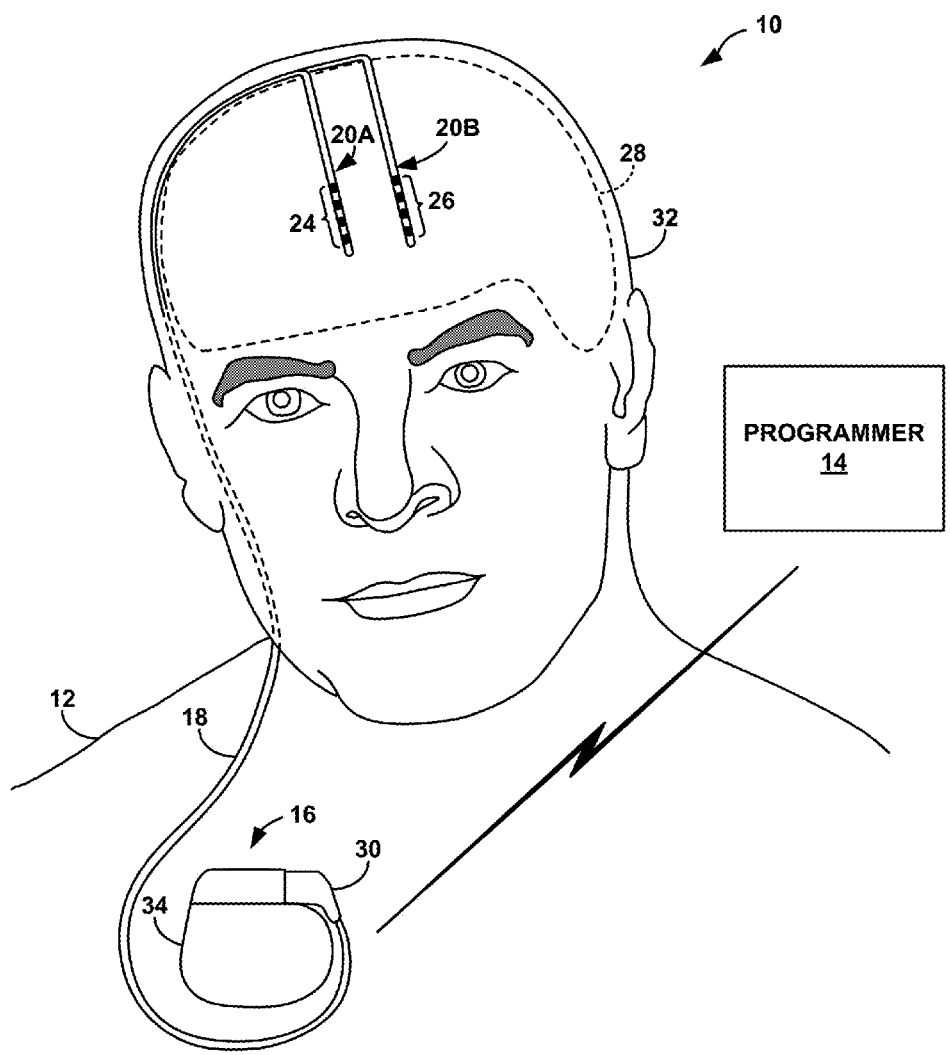
FIG. 1 is a conceptual diagram illustrating an example deep brain stimulation (DBS) system configured to sense a bioelectrical brain signal and deliver electrical stimulation therapy to a tissue site within a brain of a patient.

The disclosure describes example systems, devices, and methods for determining therapy parameters for stimulation frequency components based on characteristics of frequency components of a sensed bioelectrical signal. For example, the bioelectrical signal of a patient may be considered as a signal that includes a plurality of frequency components, where each frequency component refers to a signal having a particular frequency. For instance, the bioelectrical signal can be represented as a summation of a plurality of sinusoidal waves at different frequencies, and potentially different amplitudes and phases. In this example, each sinusoidal wave at respective frequencies may be considered as a frequency component of the bioelectrical signal.

A device such as a medical device or a programmer for a medical device may determine the characteristics of the frequency components, such as the frequencies, amplitudes, and phases of the frequency components. The device need not determine the characteristics of each of the frequency components, but may generally determine the characteristics of two or more of the frequency components.

In response to determining the characteristics of the frequency components, the device may determine therapy parameters for a stimulation signal. For example, in the techniques described in this disclosure, the stimulation signal delivered by the medical device includes a plurality of frequency components. To avoid confusion, the frequency components of the sensed bioelectrical signal are referred to as sensed frequency components, and the frequency components of the stimulation signal are referred to as stimulation frequency components.

In some examples, the device determines therapy parameters, including adjusting or controlling therapy parameters, such as amplitude and phase of a plurality of the stimulation frequency components based on the sensed frequency components (e.g., without a user providing the therapy parameters). In some examples, the device determines therapy parameters of the stimulation frequency components by receiving information indicative of the therapy parameters. For instance, in response to determining the characteristics of the sensed frequency components, the device may output information indicative of the characteristics of the sensed frequency components. The device may then receive, from a user, information indicative of the therapy parameters. In this case, the device determines the therapy parameters in the sense that the device determines the therapy parameters from the received information, and makes such a determination in response to determining the characteristics of the sensed frequency components.

The device need not necessarily determine therapy parameters for all of the stimulation frequency components based on the sensed frequency components. The device may determine the therapy parameters for two or more stimulation frequency components, and determine the therapy parameters for the other stimulation frequency components utilizing some other technique (e.g., preset therapy parameters). Also, the sensed frequency components and the stimulation frequency components need not necessarily be at the same frequencies. However, it may be possible for the sensed frequency components and the stimulation frequency components to be the same frequency.

In this manner, the device may determine the stimulation waveform in the frequency domain (i.e., based on the frequency components), rather than in a time domain (i.e., based on the pulse width). For instance, for deep brain stimulation (DBS) therapy, some techniques determine stimulation waveforms based on time domain wave shapes (e.g., rectangular pulse, triangle pulse, sine waveform, etc.). However, the malfunction of the brain may involve multiple oscillators. In other words, the sensed brain signal may not be the same as a baseline brain signal, where the baseline brain signal is a brain signal of a brain without the ailment being treated by the stimulation signal. The difference in the sensed brain signal and the baseline signal may be due to the frequency, amplitude, and/or phase of the frequency components of the sensed brain signal being different than the frequency, amplitude, and/or phase of the frequency components of the baseline brain signal. By combining different stimulation frequency components to generate a stimulation waveform, the example techniques may provide more effective and power efficient stimulation therapy as compared to stimulation therapy generated based only on time domain characteristics (e.g., a pulse width of a stimulation signal to be delivered and amount of times the stimulation signal is delivered within a certain time frame).

It should be understood that the frequency at which stimulation is delivered should not be confused with the frequency components described in this disclosure. For instance, in therapy parameters determined in the time domain, a device defines the pulse width, amplitude, and frequency of the therapy parameters. However, this frequency is how often the therapy is delivered, and is not reflective of a frequency component of the actual therapy that is delivered. As an example, the medical device may deliver therapy for one second every 10 seconds. In this example, frequency at which stimulation is delivered is 0.1 Hz (1/10 seconds). In the techniques described in this disclosure, the frequency components refer to the frequency components of the therapy that is delivered (e.g., the therapy signal may include a 5 Hz component and a 150 Hz component, as an example).

Also, although the examples described in this disclosure are described with respect to bioelectrical brain signals for DBS, the techniques described in this disclosure are not so limited. The techniques described in this disclosure may be utilized for other purposes such as spinal cord stimulation (SCS), pelvic stimulation, gastric stimulation, peripheral nerve stimulation, and functional electrical stimulation to a target tissue site within a patient.

FIG. 1 is a conceptual diagram illustrating an example therapy system 10 that is configured to deliver therapy to patient 12 to manage a disorder of patient 12. In some examples, therapy system 10 may deliver therapy to patient 12 to manage a movement disorder or a neurodegenerative impairment of patient 12. Patient 12 ordinarily will be a human patient. In some cases, however, therapy system 10 may be applied to other mammalian or non-mammalian non-human patients. A movement disorder may be characterized by one or more symptoms, such as, but not limited to, impaired muscle control, motion impairment or other movement problems, such as rigidity, bradykinesia, rhythmic hyperkinesia, nonrhythmic hyperkinesia, dystonia, tremor, and akinesia. In some cases, the movement disorder may be a symptom of Parkinson's disease or Huntington's disease. However, the movement disorder may be attributable to other patient conditions.

Although movement disorders are primarily referred to throughout the remainder of the application, in other examples, therapy system 10 may be configured to deliver therapy to manage other patient conditions, such as, but not limited to, seizure disorders (e.g., epilepsy), psychiatric disorders, behavior disorders, mood disorders, memory disorders, mentation disorders, Alzheimer's disease, or other neurological or psychiatric impairments, in addition to or instead of a movement disorder. Examples of psychiatric disorders include major depressive disorder (MDD), bipolar disorder, anxiety disorders, post traumatic stress disorder, dysthymic disorder, and obsessive compulsive disorder (OCD). Treatment of other patient disorders via delivery of therapy to brain 28 or another suitable target therapy delivery site in patient 12 is also contemplated.

In the example shown in FIG. 1, therapy system 10 includes medical device programmer 14, implantable medical device (IMD) 16, lead extension 18, and one or more leads 20A and 20B (collectively "leads 20") with respective sets of electrodes 24, 26. IMD 16 includes a therapy module that includes a stimulation generator that is configured to generate and deliver electrical stimulation therapy to one or more regions of brain 28 of patient 12 via a subset of electrodes 24, 26 of leads 20A and 20B, respectively. In the example shown in FIG. 1, therapy system 10 may be referred to as a deep brain stimulation (DBS) system because IMD 16 provides electrical stimulation therapy directly to tissue within brain 28, e.g., a tissue site under the dura mater of brain 28 or one or more branches or nodes, or a confluence of fiber tracks. In other examples, leads 20 may be positioned to deliver therapy to a surface of brain 28 (e.g., the cortical surface of brain 28). In some examples, IMD 16 may provide cortical stimulation therapy to patient 12, e.g., by delivering electrical stimulation to one or more tissue sites in the cortex of brain 28. In some examples, IMD 16 may provide vagal nerve stimulation (VNS) therapy to patient 12 by delivering electrical stimulation to one or more vagal nerve tissue sites.

In the example shown in FIG. 1, IMD 16 may be implanted within a subcutaneous pocket in the pectoral region of patient 12. In other examples, IMD 16 may be implanted within other regions of patient 12, such as a subcutaneous pocket in the abdomen or buttocks of patient 12 or proximate the cranium of patient 12. Implanted lead extension 18 is coupled to IMD 16 via connector block 30 (also referred to as a header), which may include, for example, electrical contacts that electrically couple to respective electrical contacts on lead extension 18. The electrical contacts electrically couple the electrodes 24, 26 carried by leads 20 to IMD 16. Lead extension 18 traverses from the implant site of IMD 16 within a chest cavity of patient 12, along the neck of patient 12 and through the cranium of patient 12 to access brain 28. IMD 16 can be constructed of a biocompatible material that resists corrosion and degradation from bodily fluids. IMD 16 may comprise a hermetic housing 34 to substantially enclose components, such as a processor, therapy module, and memory.

In the example shown in FIG. 1, leads 20 are implanted within the right and left hemispheres, respectively, of brain 28 in order to deliver electrical stimulation to one or more regions of brain 28, which may be selected based on many factors, such as the type of patient condition for which therapy system 10 is implemented to manage. Other implant sites for leads 20 and IMD 16 are contemplated. For example, IMD 16 may be implanted on or within cranium 32 or leads 20 may be implanted within the same hemisphere at multiple target tissue sites or IMD 16 may be coupled to a single lead that is implanted in one or both hemispheres of brain 28.

Leads 20 may be positioned to deliver electrical stimulation to one or more target tissue sites within brain 28 to manage patient symptoms associated with a disorder of patient 12. Leads 20 may be implanted to position electrodes 24, 26 at desired locations of brain 28 through respective holes in cranium 32. Leads 20 may be placed at any location within brain 28 such that electrodes 24, 26 are capable of providing electrical stimulation to target tissue sites within brain 28 during treatment. Different neurological or psychiatric disorders may be associated with activity in one or more of regions of brain 28, which may differ between patients. For example, a suitable target therapy delivery site within brain 28 for controlling a movement disorder of patient 12 may include one or more of the pedunculopontine nucleus (PPN), thalamus, basal ganglia structures (e.g., globus pallidus, substantia nigra or subthalamic nucleus), zona inserta, fiber tracts, lenticular fasciculus (and branches thereof), ansa lenticularis, and/or the Field of Forel (thalamic fasciculus). The PPN may also be referred to as the pedunculopontine tegmental nucleus.

As another example, in the case of MDD, bipolar disorder, OCD, or other anxiety disorders, leads 20 may be implanted to deliver electrical stimulation to the anterior limb of the internal capsule of brain 28, and only the ventral portion of the anterior limb of the internal capsule (also referred to as a VC/VS), the subgenual component of the cingulate cortex (which may be referred to as CG25), anterior cingulate cortex Brodmann areas 32 and 24, various parts of the prefrontal cortex, including the dorsal lateral and medial pre-frontal cortex (PFC) (e.g., Brodmann area 9), ventromedial prefrontal cortex (e.g., Brodmann area 10), the lateral and medial orbitofrontal cortex (e.g., Brodmann area 11), the medial or nucleus accumbens, thalamus, intralaminar thalamic nuclei, amygdala, hippocampus, the lateral hypothalamus, the Locus ceruleus, the dorsal raphe nucleus, ventral tegmentum, the substantia nigra, subthalamic nucleus, the inferior thalamic peduncle, the dorsal medial nucleus of the thalamus, the habenula, the bed nucleus of the stria terminalis, or any combination thereof. Target tissue sites not located in brain 28 of patient 12 are also contemplated.

As another example, in the case of a seizure disorder or Alzheimer's disease, for example, leads 20 may be implanted to deliver electrical stimulation to regions within the Circuit of Papez, such as, e.g., the anterior thalamic nucleus, the internal capsule, the cingulate, the fornix, the mammillary bodies, the mammillothalamic tract (mammillothalamic fasciculus), and/or hippocampus. For example, in the case of a seizure disorder, IMD 16 may deliver therapy to a region of brain 28 via a selected subset of electrodes 24, 26 to suppress cortical activity within the anterior thalamic nucleus, hippocampus, or other brain region associated with the occurrence of seizures (e.g., a seizure focus of brain 28).

Conversely, in the case of Alzheimer's disease, IMD 16 may deliver therapy to a region of brain 28 via electrodes 24, 26 to increase cortical activity within the anterior thalamic nucleus, hippocampus, or other brain region associated with Alzheimer's disease. As another example, in the case of depression (e.g., MDD), IMD 16 may deliver therapy to a region of brain 28 via electrodes 24, 26 to increase cortical activity within one or more regions of brain 28 to effectively treat the patient disorder. As another example, IMD 16 may deliver therapy to a region of brain 28 via electrodes 24, 26 to decrease cortical activity within one or more regions of brain 28, such as, e.g., the frontal cortex, to treat the disorder.

Although leads 20 are shown in FIG. 1 as being coupled to a common lead extension 18, in other examples, leads 20 may be coupled to IMD 16 via separate lead extensions or directly coupled to IMD 16. Moreover, although FIG. 1 illustrates system 10 as including two leads 20A and 20B coupled to IMD 16 via lead extension 18, in some examples, system 10 may include one lead or more than two leads.

Leads 20 may be implanted within a desired location of brain 28 via any suitable technique, such as through respective burr holes in the skull of patient 12 or through a common burr hole in the cranium 32. Leads 20 may be placed at any location within brain 28 such that electrodes 24, 26 of leads 20 are capable of providing electrical stimulation to targeted tissue during treatment. Electrical stimulation generated from the stimulation generator (not shown) within the therapy module of IMD 16 may help mitigate the symptoms of movement disorders, such as by improving the performance of motor tasks by patient 12 that may otherwise be difficult. These tasks may include, for example, at least one of initiating movement, maintaining movement, grasping and moving objects, improving gait and balance associated with narrow turns, and the like. The exact therapy parameter values of the electrical stimulation therapy that may help mitigate symptoms of the movement disorder (or other patient condition) may be specific for the particular target stimulation site (e.g., the region of the brain) involved as well as the particular patient and patient condition.

In the examples shown in FIG. 1, electrodes 24, 26 of leads 20 are shown as ring electrodes. Ring electrodes may be relatively easy to program and are typically capable of delivering an electrical field to any tissue adjacent to leads 20. In other examples, electrodes 24, 26 of leads 20 may have different configurations. For example, electrodes 24, 26 of leads 20 may have a complex electrode array geometry that is capable of producing shaped electrical fields, including interleaved stimulation. An example of a complex electrode array geometry, may include an array of electrodes positioned at different axial positions along the length of a lead, as well as at different angular positions about the periphery, e.g., circumference, of the lead. The complex electrode array geometry may include multiple electrodes (e.g., partial ring or segmented electrodes) around the perimeter of each lead 20, in addition to, or instead of, a ring electrode. In this manner, electrical stimulation may be directed to a specific direction from leads 20 to enhance therapy efficacy and reduce possible adverse side effects from stimulating a large volume of tissue. In some examples in which multiple leads 20 are implanted on the same hemisphere surrounding a target, steered electrical stimulation can be performed in between two or more electrodes.

In some examples, outer housing 34 of IMD 16 may include one or more stimulation and/or sensing electrodes. For example, housing 34 can comprise an electrically conductive material that is exposed to tissue of patient 12 when IMD 16 is implanted in patient 12, or an electrode can be attached to housing 34. In other examples, leads 20 may have shapes other than elongated cylinders as shown in FIG. 1 with active or passive tip configurations. For example, leads 20 may be paddle leads, spherical leads, bendable leads, or any other type of shape effective in treating patient 12.

IMD 16 may deliver electrical stimulation therapy to brain 28 of patient 12 according to one or more stimulation therapy programs. A stimulation therapy program may define one or more electrical stimulation parameter values for therapy generated by a therapy module of IMD 16 and delivered from IMD 16 to brain 28 of patient 12. Where IMD 16 delivers electrical stimulation in the form of electrical pulses, for example, the electrical stimulation parameters may include amplitude (constant current or constant voltage), pulse amplitude, pulse width, a waveform shape, a plurality of frequency components, etc. In addition, if different electrodes are available for delivery of stimulation, a therapy parameter of a therapy program may be further characterized by an electrode combination, which may define selected electrodes and their respective polarities.

In some examples, IMD 16 is configured to deliver electrical stimulation therapy to brain 28 of patient 12 in an open loop manner, in which IMD 16 delivers the stimulation therapy without intervention from a user or a sensor. In other examples, IMD 16 is configured to deliver electrical stimulation therapy to brain 28 of patient 12 in a closed loop manner, in which IMD 16 controls the timing of the delivery of electrical stimulation to brain 28, the output parameters of the electrical stimulation, or both based on one or more of user input and input from a sensor. The sensor may, for example, provide feedback that may be used to control the electrical stimulation output from IMD 16.

In addition to being configured to deliver therapy to manage a disorder of patient 12, therapy system 10 is configured to sense bioelectrical signals of patient 12 (e.g., bioelectrical brain signals in the example of FIG. 1). For example, IMD 16 may include a sensing module that is configured to sense bioelectrical signals within one or more regions of brain 28 via a subset of electrodes 24, 26, another set of electrodes, or both. Accordingly, in some examples, electrodes 24, 26 may be used to deliver electrical stimulation from the therapy module to target sites within brain 28 as well as sense brain signals within brain 28. However, IMD 16 can also use a separate set of sensing electrodes to sense the bioelectrical brain signals. In the example shown in FIG. 1, the signals generated by electrodes 24, 26 are conducted to the sensing module within IMD 16 via conductors within the respective lead 20A, 20B. In some examples, the sensing module of IMD 16 may sense bioelectrical signals via one or more of the electrodes 24, 26 that are also used to deliver electrical stimulation to brain 28. In other examples, one or more of electrodes 24, 26 may be used to sense bioelectrical signals while one or more different electrodes 24, 26 may be used to deliver electrical stimulation.

Depending on the particular stimulation electrodes and sense electrodes used by IMD 16, IMD 16 may monitor bioelectrical signals and deliver electrical stimulation at the same region of brain 28 or at different regions of brain 28. In some examples, the electrodes used to sense bioelectrical signals may be located on the same lead used to deliver electrical stimulation, while in other examples, the electrodes used to sense bioelectrical signals may be located on a different lead than the electrodes used to deliver electrical stimulation. In some examples, a bioelectrical signal of patient 12 may be monitored with external electrodes, e.g., scalp electrodes. Moreover, in some examples, the sensing module that senses bioelectrical signals of brain 28 (e.g., the sensing module that generates an electrical signal indicative of the activity within brain 28) is in a physically separate housing from outer housing 34 of IMD 16. However, in the example shown in FIG. 1 and the example primarily referred to herein for ease of description, the sensing module and therapy module of IMD 16 are enclosed within a common outer housing 34.

The bioelectrical signals sensed by IMD 16 may reflect changes in electrical current produced by the sum of electrical potential differences across brain tissue. Example bioelectrical brain signals include, but are not limited to, an electroencephalogram (EEG) signal, an electrocorticogram (ECoG) signal, a local field potential (LFP) sensed from within one or more regions of a patient's brain, and/or action potentials from single cells within the patient's brain. In some examples, LFP data can be measured ipsilaterally or contralaterally and considered as an average (e.g., a maximum or minimum or a heuristic combination thereof) or as some other value. The location at which the signals are obtained may be adjusted to a disease onset side of the body of patient 12 or severity of symptoms or disease duration. The adjustments, may, for example, be made on the basis of clinical symptoms presented and their severity, which can be augmented or annotated with recorded LFP data. A clinician or a processor of IMD 16 may also add heuristic weights to ipsilaterally and/or contralaterally measured LFP data to be considered for system feedback.

External programmer 14 is configured to wirelessly communicate with IMD 16 as needed to provide or retrieve therapy information. Programmer 14 is an external computing device that the user, e.g., the clinician and/or patient 12, may use to communicate with IMD 16. For example, programmer 14 may be a clinician programmer that the clinician uses to communicate with IMD 16 and program one or more therapy programs for IMD 16. In addition, or instead, programmer 14 may be a patient programmer that allows patient 12 to select programs and/or view and modify therapy parameter values. The clinician programmer may include more programming features than the patient programmer. In other words, more complex or sensitive tasks may only be allowed by the clinician programmer to prevent an untrained patient from making undesired changes to IMD 16.

Programmer 14 may be a hand-held computing device with a display viewable by the user and an interface for providing input to programmer 14 (i.e., a user input mechanism). For example, programmer 14 may include a small display screen (e.g., a liquid crystal display (LCD) or a light emitting diode (LED) display) that presents information to the user. In addition, programmer 14 may include a touch screen display, keypad, buttons, a peripheral pointing device or another input mechanism that allows the user to navigate through the user interface of programmer 14 and provide input. If programmer 14 includes buttons and a keypad, the buttons may be dedicated to performing a certain function, i.e., a power button, the buttons and the keypad may be soft keys that change in function depending upon the section of the user interface currently viewed by the user, or any combination thereof. Alternatively, the screen (not shown) of programmer 14 may be a touch screen that allows the user to provide input directly to the user interface shown on the display. The user may use a stylus or their finger to provide input to the display.

In other examples, programmer 14 may be a larger workstation or a separate application within another multi-function device, rather than a dedicated computing device. For example, the multi-function device may be a notebook computer, tablet computer, workstation, cellular phone, personal digital assistant or another computing device that may run an application that enables the computing device to operate as a secure medical device programmer 14. A wireless adapter coupled to the computing device may enable secure communication between the computing device and IMD 16.

When programmer 14 is configured for use by the clinician, programmer 14 may be used to transmit initial programming information to IMD 16. This initial information may include hardware information, such as the type of leads 20, the arrangement of electrodes 24, 26 on leads 20, the position of leads 20 within brain 28, initial programs defining therapy parameter values, and any other information that may be useful for programming into IMD 16. Programmer 14 may also be capable of completing functional tests (e.g., measuring the impedance of electrodes 24, 26 of leads 20).

The clinician may also generate and store therapy programs within IMD 16 with the aid of programmer 14. During a programming session, the clinician may determine one or more therapy programs that may provide efficacious therapy to patient 12 to address symptoms associated with the movement disorder (or other patient conditions). For example, the clinician may select one or more electrode combinations with which stimulation is delivered to brain 28. During the programming session, patient 12 may provide feedback to the clinician as to the efficacy of the specific program being evaluated or the clinician may evaluate the efficacy based on one or more sensed or observable physiological parameters of patient (e.g., muscle activity) or based on motion detected via one or more motion sensors that generate signals indicative of motion of patient 12. Programmer 14 may assist the clinician in the creation/identification of therapy programs by providing a methodical system for identifying potentially beneficial therapy parameter values.

Programmer 14 may also be configured for use by patient 12. When configured as a patient programmer, programmer 14 may have limited functionality (compared to a clinician programmer) in order to prevent patient 12 from altering critical functions of IMD 16 or applications that may be detrimental to patient 12.

Whether programmer 14 is configured for clinician or patient use, programmer 14 is configured to communicate to IMD 16 and, optionally, another computing device, via wireless communication. Programmer 14, for example, may communicate via wireless communication with IMD 16 using radio frequency (RF) telemetry techniques known in the art. Programmer 14 may also communicate with another programmer or computing device via a wired or wireless connection using any of a variety of local wireless communication techniques, such as RF communication according to the 802.11 or Bluetooth specification sets, infrared (IR) communication according to the IRDA specification set, or other standard or proprietary telemetry protocols. Programmer 14 may also communicate with other programming or computing devices via exchange of removable media, such as magnetic or optical disks, memory cards or memory sticks. Further, programmer 14 may communicate with IMD 16 and another programmer via remote telemetry techniques known in the art, communicating via a local area network (LAN), wide area network (WAN), public switched telephone network (PSTN), or cellular telephone network, for example.

In accordance with the example techniques described in this disclosure, IMD 16 receives information representative of a bioelectrical signal of patient 12. For instance, electrodes 24, 26 may sense a bioelectrical signal and transmit a voltage signal representative of the bioelectrical signal to IMD 16. This bioelectrical signal includes a plurality of frequency components. For example, the bioelectrical signal is equivalent to summing a plurality of waveforms (e.g., as defined by basis functions, such as sine wave basis functions), where each waveform has a different frequency and a different weight that determines the amplitude of the waveform at the particular frequency. In other words, a frequency component, as used in this disclosure, refers to a constituent waveform having a specific frequency that when summed together with the other frequency components results in the bioelectrical signal. The frequencies of the constituent waveforms may be different, the amplitudes of the constituent waveforms may be different, and the phases of the constituent waveforms may be different.

Figure 2:
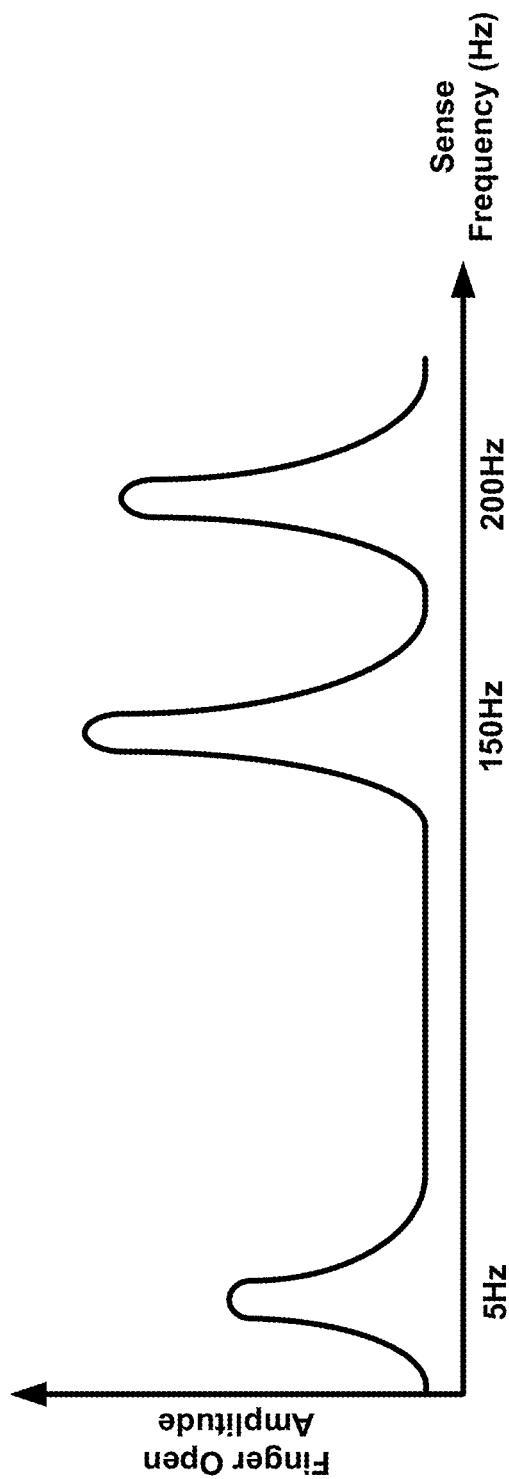
FIG. 2 is an example of finger opening amplitude versus sensed frequency.

For example, FIG. 2 is an example of a finger opening amplitude versus sensed frequency. In particular, FIG. 2 illustrates the finger opening amplitude for a patient with Parkinson's disease (i.e., PD patient) with respect to the sensed frequency components. As illustrated, the sensed signal includes a plurality of frequency components centered around approximately 5 Hz, approximately 150 Hz, and approximately 200 Hz. The amplitude of the 5 Hz frequency component is less than the amplitudes of both the 150 Hz frequency component and the 200 Hz frequency component. The amplitude of the 150 Hz frequency component is the greatest amplitude, with the amplitude of the 200 Hz frequency component being in between the amplitudes of the 150 Hz and 5 Hz frequency components. Accordingly, FIG. 2 illustrates different relative peaks at multiple frequencies in the sensed signal.

In this example, the actual brain signal in the time domain does not appear as illustrated in FIG. 2. Rather, conceptually, the example illustrated in FIG. 2 is a result of a frequency spectrum analysis of the brain signal sensed by electrodes 24, 26. In this example, the 5 Hz, 150 Hz, and 200 Hz frequency components may be summed together at their respective amplitudes and phases to reconstruct the brain signal.

Referring back to FIG. 1, IMD 16 may receive information representative of the bioelectrical signal (e.g., the voltage signal) and determine characteristics of two or more sensed frequency components of a plurality of sensed frequency components, where the plurality of sensed frequency components together forms the bioelectrical signal. Examples of the characteristics of the sensed frequency components include an amplitude and/or phase.

For instance, IMD 16 may determine the sensed frequency components at which relative peak amplitudes exist in the bioelectrical signal. In the example of FIG. 2, IMD 16 may determine that, for the 5 Hz, 150 Hz, and 200 Hz sensed frequency components, there exists amplitude peaks in the bioelectrical signal. IMD 16 may additionally or alternatively determine the phases of the sensed frequency components (e.g., determine the phases of the 5 Hz, 150 Hz, and 200 Hz sensed frequency components). It should be understood that although the preceding example describes IMD 16 determining characteristics for all of the frequency components, aspects of this disclosure are not so limited. In some examples, IMD 16 may determine characteristics of fewer than all of the frequency components (e.g., two or more of the plurality of frequency components). For instance, IMD 16 may determine characteristics of any two of three frequency components illustrated in FIG. 2.

In response to determining the characteristics of the two or more sensed frequency components, IMD 16 may determine therapy parameters for two or more stimulation frequency components of a plurality of stimulation frequency components of a stimulation signal. For instance, in the techniques described in this disclosure, the stimulation that IMD 16 outputs includes a plurality of frequency components (referred to as stimulation frequency components to avoid confusion with sensed frequency components). Examples of the therapy parameters include the amplitude and/or phase of the stimulation frequency components. The stimulation signal (e.g., stimulation therapy) that IMD 16 outputs equals the summation of each of the stimulation frequency components at their respective frequencies, amplitudes, and phases.

In some examples, IMD 16 may determine the therapy parameters based on the characteristics of the sensed frequency components. As an example, IMD 16 may determine that the amplitude of sensed 200 Hz frequency component is too low, and in response, may determine the amplitude for a 200 Hz stimulation frequency component to increase the amplitude of the 200 Hz frequency component. IMD 16 may need to similarly determine a phase of the 200 Hz stimulation frequency component so that it is additive with the natural existing 200 Hz frequency component in bioelectrical brain signal. In this example, by increasing the amplitude of the 200 Hz frequency component (e.g., adding to the natural existing 200 Hz frequency component), IMD 16 may be address a patient condition for which having a signals greater than a threshold at 200 Hz provides symptom relief.

As another example, IMD 16 may determine an amplitude for a 200 Hz stimulation frequency component that is the same as the amplitude of the 200 Hz sensed frequency component, but may determine the phase of the 200 Hz stimulation frequency component to be 180° out-of-phase with the stimulation frequency. In this case, the stimulation frequency component may subtract from the natural existing frequency component. In this way, IMD 16 may disrupt and squelch a brain signal the existence of which is causing discomfort.

Although the above examples describe that IMD 16 determines amplitude and/or phase for a stimulation frequency component having the same frequency as a sensed frequency component, the techniques described in this disclosure are not so limited. In some examples, based on a sensed frequency component, IMD 16 may determine the amplitude and/or phase of a stimulation frequency component having a different frequency as the sensed frequency component. In general, it is the characteristics of the sensed frequency component from which IMD 16 determines the characteristics of the stimulation frequency component, whether the sensed frequency component and the stimulation frequency component are the same or different.

In the above example, IMD 16 was described as the unit that performs the techniques described in this disclosure. However, in some examples, programmer 14 alone or in combination with IMD 16 may perform the techniques described in this disclosure. For example, IMD 16 may receive, from electrodes 24, 26, a voltage signal of the bioelectrical signal of patient 12. IMD 16 may then transmit information representative of the bioelectrical signal, and programmer 14 may receive information representative of the bioelectrical signal of patient 12. Programmer 14 may then determine characteristics of two or more of the sensed frequency components, and determine therapy parameters for two or more of the stimulation frequency components as described above with IMD 16.

In some examples, IMD 16 may determine the characteristics of two or more of the sensed frequency components and output information to programmer 14 regarding the characteristics. In turn, programmer 14 may determine the therapy parameters. As another example, programmer 14 may determine characteristics of two or more of the sensed frequency components and transmit information to IMD 16 regarding the characteristics. In turn, IMD 16 may determine the therapy parameters. In this manner, IMD 16 or programmer 14, either alone or in combination, may perform example techniques described in this disclosure.

As described above, IMD 16 and/or programmer 14 may perform example techniques described in this disclosure without user intervention. However, the techniques are not so limited. In some examples, after IMD 16 or programmer 14 determines characteristics of sensed frequency components, programmer 14 may output information indicative of the characteristics. The clinician or patient may review the characteristics of the sensed frequency components, and provide information indicative of the therapy parameters. In this example, programmer 14 receives information indicative of the therapy parameters in response to outputting information indicative of the determined characteristics. Accordingly, in this example, programmer 14 may determine the therapy parameters based on the received information indicative of the therapy parameters.

Furthermore, in examples where IMD 16 and/or programmer 14 determine the therapy parameters without user intervention, programmer 14 may still output information indicative of the determined therapy parameters for user confirmation. For instance, in some cases, the clinician may modify the determined therapy parameters or otherwise confirm that the therapy parameters are satisfactory (e.g., not violating a threshold level). In examples where the clinician, or maybe even patient 12, modifies the therapy parameters, programmer 14 may output information to IMD 16 indicating the modified therapy parameters of the stimulation frequency components.

In any event, IMD 16 and/or programmer 14 may cause a stimulation generator of IMD 16 to deliver (e.g., output) the stimulation signal (e.g., stimulation therapy). In this manner, IMD 16 may deliver a stimulation signal that includes a plurality of frequency components determined in the frequency domain (i.e., characteristics of the sensed frequency components). Because the bioelectrical signals may be better modeled using a plurality of frequency components, stimulation that is generated based on a plurality of frequency components may provide more efficacious therapy as compared to other stimulations that are not generated based on frequency components.

In another example, the medical device (e.g., IMD 16) or programmer 14 can distinguish between different brain states, such as a desired state (e.g., treated or healthy) versus a non-desirable state (e.g., untreated). IMD 16 may deliver stimulation therapy in the manner described in this disclosure during the desired state. If IMD 16 or programmer 14 detect the signal frequency components of a non-desirable state, IMD 16 may be configured to deliver the stimulation therapy previously associated with the desired state. In some examples, IMD 16 or programmer 14 may utilize the sensed frequency components to generate a stimulation waveform that is out of phase with the sensed signal at the particular sensed frequencies with the aim to interfere or abolish the non-desirable state.

For example, IMD 16 or programmer 14 may determine that a patient state of patient 12 is an untreated state based on the characteristics of the sensed frequency components. In this example, IMD 16 or programmer 14 may determine therapy parameters that are associated with a treated state for the patient state of patient 12 based on the determination that the patient state is the untreated state.

As another example, IMD 16 or programmer 14 may determine phases of the sensed frequency components, where the phases are examples of the characteristics of the sensed frequency components. IMD 16 or programmer 14 may determine phases of the frequency components of the stimulation signal that are out of phase with the determined phases of the sensed frequency components. For instance, the phases of the frequency components of the stimulation signal may be selected to be 180° out of phase with the determined phases of the sensed frequency components so that the stimulation signal has the effect of canceling the sensed frequency components.

Therapy system 10 may be implemented to provide chronic stimulation therapy to patient 12 over the course of several months or years. However, system 10 may also be employed on a trial basis to evaluate therapy before committing to full implantation. If implemented temporarily, some components of system 10 may not be implanted within patient 12. For example, patient 12 may be fitted with an external medical device, such as a trial stimulator, rather than IMD 16. The external medical device may be coupled to percutaneous leads or to implanted leads via a percutaneous extension. If the trial stimulator indicates DBS system 10 provides effective treatment to patient 12, the clinician may implant a chronic stimulator within patient 12 for relatively long-term treatment.

System 10 shown in FIG. 1 is merely one example of a therapy system that is configured to perform the techniques described in this disclosure. Systems with other configurations of leads, electrodes, and sensors are possible. For example, in other implementations, IMD 16 may be coupled to additional leads or lead segments having one or more electrodes positioned at different target tissue sites, which may be within brain 28 or outside of the brain (e.g., proximate to a spinal cord of patient 12, a peripheral nerve of patient 12, a muscle of patient 12, or any other suitable therapy delivery site). The additional leads may be used for delivering different stimulation therapies to respective stimulation sites within patient 12 or for monitoring at least one physiological parameter of patient 12.

Additionally, in other examples, a system may include more than one IMD. For example, a system may include two IMDs coupled to respective one or more leads. Each IMD can deliver stimulation to a respective lateral side of patient 12 in some examples.

As another example configuration, a therapy system can include one or more leadless electrical stimulators (e.g., microstimulators having a smaller form factor than IMD 16 and may not be coupled to any separate leads). The leadless electrical stimulators can be configured to generate and deliver electrical stimulation therapy to patient 12 via one or more electrodes on an outer housing of the electrical stimulator. In examples including a plurality of leadless electrical stimulators, the leadless electrical stimulators can be implanted at different target tissue sites within patient 12. One electrical stimulator may act as a "master" module that coordinates the delivery of stimulation to patient 12 via the plurality of electrical stimulators.

In some examples, IMD 16 is not configured to deliver electrical stimulation therapy to brain of patient 12, but, rather, is only configured to sense one or more physiological parameters of patient 12, including a bioelectrical brain signal of patient 12. This type of IMD 16 may be a patient monitoring device useful for diagnosing patient 12, monitoring a patient condition 12, or to train IMD 16 or another IMD for therapy delivery.

Figure 3:
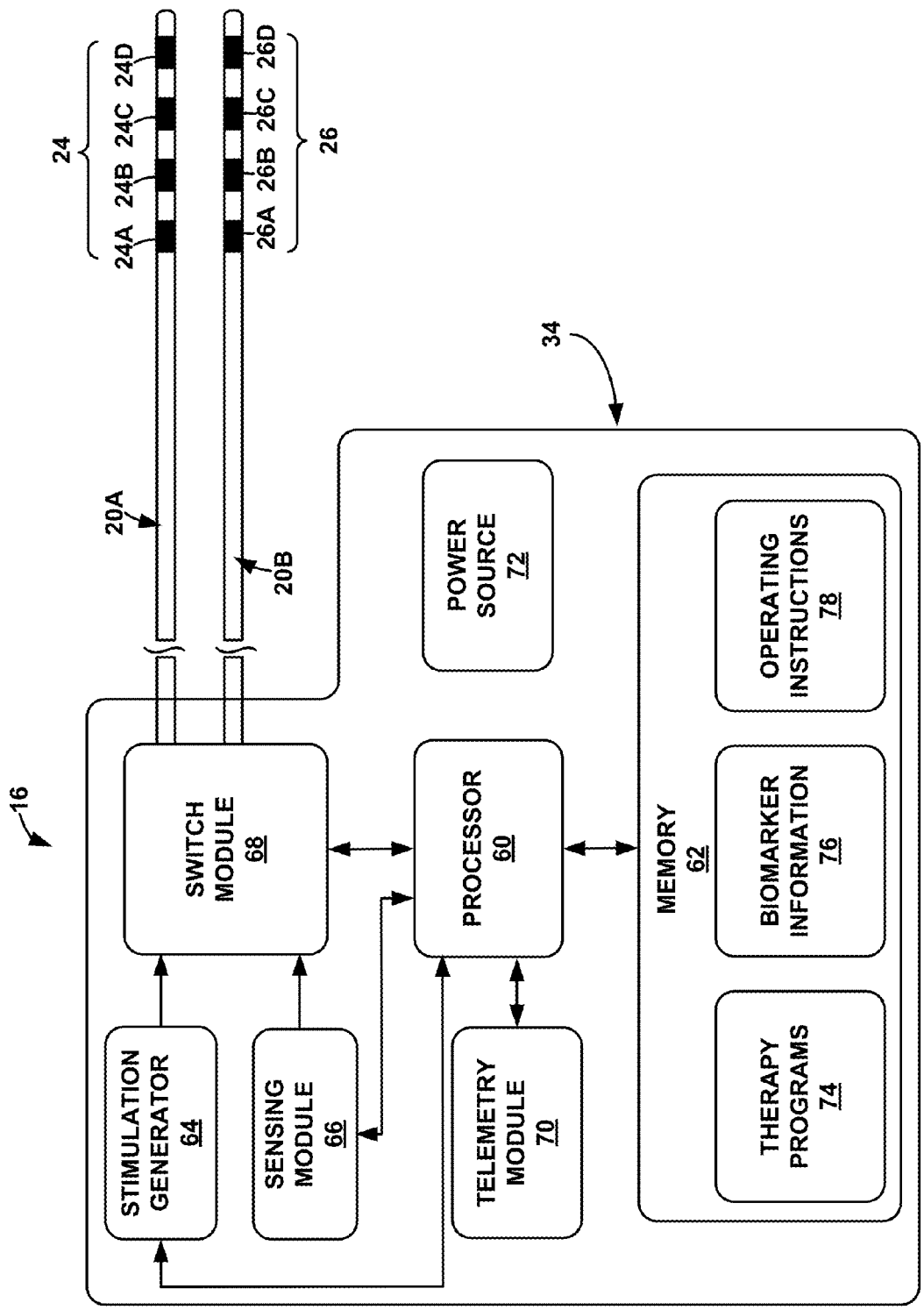
FIG. 3 is functional block diagram illustrating components of an example medical device.

FIG. 3 is functional block diagram illustrating components of an example IMD 16. In the example shown in FIG. 2, IMD 16 includes processor 60, memory 62, stimulation generator 64, sensing module 66, switch module 68, telemetry module 70, and power source 72. Memory 62, as well as other memories described herein, may include any volatile or non-volatile media, such as a random access memory (RAM), read only memory (ROM), non-volatile RAM (NVRAM), electrically erasable programmable ROM (EEPROM), flash memory, and the like. Memory 62 may store computer-readable instructions that, when executed by processor 60, cause IMD 16 to perform various functions described herein.

In the example shown in FIG. 2, memory 62 stores therapy programs 74, biomarker information 76, and operating instructions 78, e.g., in separate memories within memory 62 or separate areas within memory 62. Each stored therapy program 74 defines a particular program of therapy in terms of respective values for electrical stimulation parameters, such as a stimulation electrode combination, electrode polarity, current or voltage amplitude, and, if stimulation generator 64 generates and delivers stimulation pulses, the therapy programs may define values for a pulse width, and pulse rate of a stimulation signal.

In accordance with the techniques described in this disclosure, the stimulation signal includes a plurality of frequency components. Each stored therapy program 74 may store the frequency, amplitude, and phase of each of the frequency components. Stored therapy programs 74 may also be referred to as a set of therapy parameter values. In some examples, the therapy programs may be stored as a therapy group, which defines a set of therapy programs with which stimulation may be generated. The stimulation signals defined by the therapy programs of the therapy group may be delivered together on an overlapping or non-overlapping (e.g., time-interleaved) basis.

Biomarker information 76 stored by memory 62 may include a baseline bioelectrical signal. The baseline bioelectrical signal may include frequency component information for frequency components of a bioelectrical signal of an individual who does not suffer from the condition that the stimulation therapy is to be address. In some examples, processor 60 or processor of another device, such as programmer 14, may determine therapy parameters for the stimulation frequency components based on the baseline bioelectrical signal stored as biomarker information 76.

For example, processor 60 may determine the characteristics of the sensed frequency components (e.g., amplitude and/or phase). Processor 60 may compare the amplitude and/or phase the baseline bioelectrical signal data stored as biomarker information 76. If biomarker information 76 indicates that a particular sensed frequency component should not exist (or should be minimized), processor 60 may determine therapy parameters for a stimulation frequency component that would disrupt the natural existing frequency component that was sensed (e.g., same amplitude, but 180° out of phase with sensed frequency component). As another example, if biomarker information 76 indicates that the amplitude of a particular sensed frequency component is too low, processor 60 may determine therapy parameters for a stimulation frequency component that would be additive with the natural existing frequency component. There may be other ways in which processor 60 may utilize biomarker information 76, and the techniques described in this disclosure are not limited to any specific example.

In some examples, memory 62 may also store brain signal data generated by sensing module 66 via at least one of electrodes 24, 26 and, in some cases, an electrode on outer housing 34 of IMD 16. In addition, in some examples, processor 60 may append a time and date stamp to the brain signal data in memory 62. Operating instructions 78 guide general operation of IMD 16 under control of processor 60, and may include instructions for monitoring brain signals within one or more brain regions via electrodes 24, 26 and delivering electrical stimulation therapy to patient 12.

Stimulation generator 64, under the control of processor 60, generates stimulation signals for delivery to patient 12 via selected combinations of electrodes 24, 26. In some examples, stimulation generator 64 generates and delivers stimulation signals to one or more target regions of brain 28 (FIG. 1), via a select combination of electrodes 24, 26, based on one or more stored therapy programs 74. The target tissue sites within brain 28 for stimulation signals or other types of therapy and stimulation parameter values may depend on the patient condition for which therapy system 10 is implemented to manage. While stimulation pulses are described, stimulation signals may be of any form, such as continuous-time signals (e.g., sine waves) or the like. In the techniques described in this disclosure, the stimulation signals include a plurality of stimulation frequency components (e.g., waveforms having different frequencies).

The processors described in this disclosure, including processor 60, may include one or more digital signal processors (DSPs), general purpose microprocessors, application specific integrated circuits (ASICs), field programmable logic arrays (FPGAs), or other equivalent integrated or discrete logic circuitry, or combinations thereof. The functions attributed to processors described herein may be provided by a hardware device and embodied as software, firmware, hardware, or any combination thereof. Processor 60 is configured to control stimulation generator 64 according to therapy programs 74 stored by memory 62 to apply particular stimulation parameter values specified by one or more programs.

In the example shown in FIG. 2, the set of electrodes 24 of lead 20A includes electrodes 24A, 24B, 24C, and 24D, and the set of electrodes 26 of lead 20B includes electrodes 26A, 26B, 26C, and 26D. Processor 60 may control switch module 68 to apply the stimulation signals generated by stimulation generator 64 to selected combinations of electrodes 24, 26. In particular, switch module 68 may couple stimulation signals to selected conductors within leads 20, which, in turn, deliver the stimulation signals across selected electrodes 24, 26. Switch module 68 may be a switch array, switch matrix, multiplexer, or any other type of switching module configured to selectively couple stimulation energy to selected electrodes 24, 26 and to selectively sense bioelectrical brain signals with selected electrodes 24, 26. Hence, stimulation generator 64 is coupled to electrodes 24, 26 via switch module 68 and conductors within leads 20. In some examples, however, IMD 16 does not include switch module 68.

Switch module 68 is illustrated as merely one example. In some examples, IMD 16 may not include switch module 68.

Rather, IMD 16 may include a plurality of stimulation sources such as current sources that sink or source current and/or a voltage sources that output a positive or a negative voltage. In such examples, each one of electrodes 24, 26 may be coupled to separate ones of the stimulation sources. In some examples, some of electrodes 24, 26 may be coupled to the same stimulation source, and others to another stimulation source, with the possibility that one stimulation source couples to a plurality of electrodes 24, 26. In examples where IMD 16 does not include switch module 68, processor 60 and/or stimulation generator 64 may selectively enable stimulation sources to delivery the stimulation. In some examples, in addition to including a plurality of stimulation sources for one or more electrodes 24, 26, IMD 16 may include switch module 68.

Stimulation generator 64 may be a single channel or multi-channel stimulation generator. In particular, stimulation generator 64 may be capable of delivering, a single stimulation pulse, multiple stimulation pulses or continuous signal including a plurality of frequency components at a given time via a single electrode combination or multiple stimulation pulses at a given time via multiple electrode combinations. In some examples, however, stimulation generator 64 and switch module 68 may be configured to deliver multiple channels on a time-interleaved basis. For example, switch module 68 may serve to time divide the output of stimulation generator 64 across different electrode combinations at different times to deliver multiple programs or channels of stimulation energy to patient 12. In examples where IMD 16 includes a plurality of stimulation sources, to achieve the time-interleaved stimulation, processor 60 and/or stimulation generator 64 may selective turn on and off stimulation sources.

As one example, the stimulation signal may include three frequency components of 10 Hz, 50 Hz, and 100 Hz, as merely one example (there may be more or fewer than three frequency components and at different frequencies than this example). In this example, processor 60 and/or stimulation generator 64 may control one stimulation source to deliver stimulation that includes the 10 Hz and 50 Hz components, and control another stimulation source to deliver stimulation that includes the 100 Hz component. As another example, three electrodes may each output one of the 10 Hz, 50 Hz, and 100 Hz frequency component, or one electrode may output the stimulation having all three frequency components. Processor 60 and/or stimulation generator 64 may selective utilize the stimulation generators to deliver the stimulation signal having the different frequency components.

Sensing module 66, under the control of processor 60, is configured to sense bioelectrical signals of patient 12 via a selected subset of electrodes 24, 26 or with one or more electrodes 24, 26 and at least a portion of a conductive outer housing 34 of IMD 16, an electrode on an outer housing of IMD 16 or another reference. Processor 60 may control switch module 68 to electrically connect sensing module 66 to selected electrodes 24, 26. In this way, sensing module 66 may selectively sense bioelectrical brain signals with different combinations of electrodes 24, 26 (and/or a reference other than an electrode 24, 26). Processor 60 may monitor the efficacy of therapy delivery by IMD 16 via the sensed bioelectrical brain signals and determine whether the efficacy of therapy delivery has changed, and, in response, generate a notification (e.g., to patient 12 or patient caretaker). In some examples, processor 60 may determine therapy parameters based on the sensed bioelectrical brain signals, and delivery therapy based on the determined parameters or cause programmer 14 to output the determined therapy parameters for user approval.

Although sensing module 66 is incorporated into a common housing 34 with stimulation generator 64 and processor 60 in FIG. 3, in other examples, sensing module 66 is in a separate outer housing from outer housing 34 of IMD 16 and communicates with processor 60 via wired or wireless communication techniques. Similarly, signal generator 64 may be in the same housing or in a separate housing from outer housing 34.

As illustrated, processor 60 receives the bioelectrical signal from sensing module 66 configured to sense the bioelectrical signal via one or more of electrodes 24, 26. Processor 60 may determine characteristics of two or more sensed frequency components of a plurality of sensed frequency components of the bioelectrical signal. The plurality of sensed frequency components together forms the bioelectrical signal.

There may be various ways in which processor 60 determines characteristics of the sensed frequency components. As one example, processor 60 may perform a Fourier transform such as a fast-Fourier transform (FFT) or a discrete Fourier transform (DFT) to convert the time domain sensed brain signal into a frequency domain, and determine characteristics of the frequency components of the bioelectrical signal (i.e., characteristics of the sensed frequency components), such as relative peak voltage or current amplitudes at various frequency components, where a relative peak is when a value is greater than a threshold or when the first derivative is equal to zero with following values being less than the peak voltage or current. As another example, processor 60 may utilize a phase locked loop (PLL) to determine characteristics of frequency components. There may be other ways in which processor 60 determines characteristics of the sensed frequency components, and the techniques described in this disclosure should not be considered limited to the above examples. In general, processor 60 may determine characteristics of the two or more sensed frequency components such as amplitude and/or phase of the two or more sensed frequency components.

There are also various ways to determine phase of a sensed frequency component. Example ways for phase determination is described in U.S. Provisional Application No. 62/114,650, filed Feb. 11, 2015, and U.S. Provisional Application No. 62/083,038, filed Nov. 21, 2014, the entire content of each of which is incorporated herein by reference.

In response to determining the characteristics of the two or more sensed frequency components, processor 60 may determine therapy parameters for two or more stimulation frequency components of a plurality of stimulation frequency components of a stimulation signal. For example, processor 60 may determine amplitude and/or phase of the two or more stimulation frequency components. In some examples, processor 60 may determine therapy parameters for two or more stimulation frequency components that correspond to the two or more sensed frequency components. For instance, if processor 60 determined characteristics for three components having a first, second, and third frequency, respectively, then processor 60 may determine therapy parameters for the first, second, and third frequency components in the stimulation signal (e.g., at substantially the same frequencies as the sensed signal, but not a requirement that they be the same frequencies as the sensed signal).

As an example, processor 60 may compare the determined characteristics of the two or more sensed frequency components to a baseline signal of frequency components stored as biomarker information 76. Processor 60 may determine the therapy parameters for the two or more stimulation parameters for the two or more stimulation parameters based on the comparison. For instance, if based on the comparison, processor 60 determines that an increase in the amplitude of a specific frequency in the sensed signal is needed (i.e., the amplitude of the sensed frequency component is less than the amplitude of the frequency component indicated in the baseline signal stored as biomarker information 76), processor 60 may determine the amplitude of the corresponding frequency component in the stimulation signal (e.g., so that the stimulation signal is additive with the frequency component of the natural patient signal).

Moreover, processor 60 may determine the pulse width for each of the frequency components, and the pulse widths for respective frequency components may be different. For example, processor 60 may determine that the stimulation signal is to be delivered for 90 microseconds. In this example, processor 60 may determine for the first 60 microseconds, the stimulation signal includes a first stimulation frequency component having an amplitude of 3.2V and a second stimulation frequency component having an amplitude of 1V. Then for the remaining 30 microseconds, processor 60 may determine that the stimulation signal includes only the second stimulation frequency component having the amplitude of 3.2V. In this example, the pulse width for the first stimulation frequency component is 60 microseconds, and the pulse width for the second stimulation frequency component is 90 microseconds.

In some examples, processor 60 may determine that the stimulation signal should include the first stimulation frequency component for the first 60 microseconds, and then include the second stimulation frequency component for the next 90 microseconds. In other words, in some examples, the first stimulation frequency component and the second stimulation frequency component may overlap with one another. In some examples, the first stimulation frequency component and the second stimulation frequency component may not necessarily overlap with one another. Additionally, it may be possible for the pulse widths of the stimulation frequency components to be different, but this is not a requirement, and the pulse widths may be the same.

The above pulse width and amplitude values are provided merely to ease with understanding and should not be considered as limiting. In some examples, stimulation frequency components may be in range of 1 Hz to 500 Hz, and approximately near 130 Hz. The voltage amplitude of each frequency component may be between approximately 0.1V and 50V, such as between approximately 0.5V and approximately 20V, or approximately 5V. The current amplitude may be between approximately 0.2 mA to approximately 100 mA, such as between approximately 1 mA and approximately 40 mA, or approximately 10 mA. The pulse width may be between approximately 10 microseconds and approximately 5000 microseconds, such as between approximately 10 microseconds and approximately 1000 microseconds, or between 30 microseconds and approximately 450 microseconds.

Accordingly, in some examples, stimulation generator 64 generates electrical stimulation signals with the electrical stimulation parameters noted above. Other ranges of therapy parameters values may also be useful, and may depend on the target stimulation site within patient. While stimulation pulses are described, stimulation signals may be of any form, such as continuous-time signals (e.g., sine waves) or the like.

In some examples, processor 60 may output information indicative of the determined characteristics of the two or more sensed frequency components in response to determining the characteristics of the two or more sensed frequency components. For instance, processor 60 may output, via telemetry module 70 and to programmer 14, information indicative of the determined characteristics of the two or more sensed frequency components. Programmer 14 may determine the therapy parameters or receive from a user therapy parameters, and output information indicative of the therapy parameters to IMD 16. Processor 60 may receive, from programmer 14, information indicative of the therapy parameters in response to outputting the information indicative of the determined characteristics. In this example, processor 60 determines the therapy parameters for the two or more stimulation frequency components based on the received information.

Processor 60 may cause stimulation generator 64 to deliver the stimulation signal. In some examples, processor 60 may output information indicative of the determined therapy parameters to programmer 14. Programmer 14 may then output the information to a user, and receive from the user information for modification to the determined therapy parameters. Programmer 14 may transmit information of the modified therapy parameters to IMD 16. Processor 60 may cause stimulation generator 64 to deliver the stimulation signal based on the modified therapy parameters.

Telemetry module 70 is configured to support wireless communication between IMD 16 and an external programmer 14 or another computing device under the control of processor 60. Processor 60 of IMD 16 may receive, as updates to programs, values for various stimulation parameters such as amplitude and electrode combination, from programmer 14 via telemetry module 70. The updates to the therapy programs may be stored within therapy programs 74 portion of memory 62. Telemetry module 70 in IMD 16, as well as telemetry modules in other devices and systems described herein, such as programmer 14, may accomplish communication by RF communication techniques. In addition, telemetry module 70 may communicate with external medical device programmer 14 via proximal inductive interaction of IMD 16 with programmer 14. Accordingly, telemetry module 70 may send information to external programmer 14 on a continuous basis, at periodic intervals, or upon request from IMD 16 or programmer 14. For example, processor 60 may transmit brain state information 76 to programmer 14 via telemetry module 70.

Power source 72 delivers operating power to various components of IMD 16. Power source 72 may include a small rechargeable or non-rechargeable battery and a power generation circuit to produce the operating power. Recharging may be accomplished through proximal inductive interaction between an external charger and an inductive charging coil within IMD 16. In some examples, power requirements may be small enough to allow IMD 16 to utilize patient motion and implement a kinetic energy-scavenging device to trickle charge a rechargeable battery. In other examples, traditional batteries may be used for a limited period of time.

Figure 4:
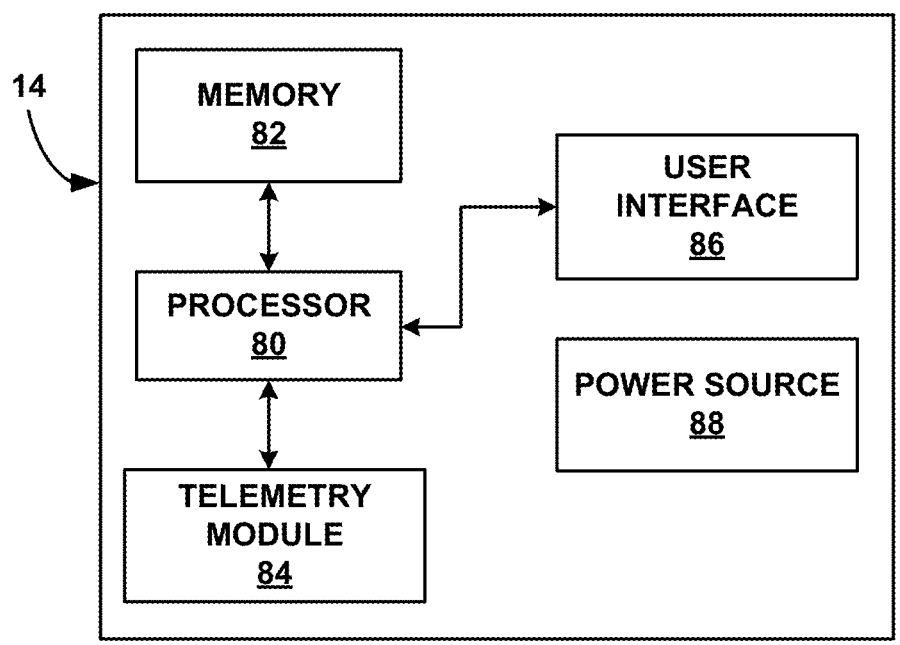
FIG. 4 is a functional block diagram illustrating components of an example medical device programmer.

FIG. 4 is a functional block diagram illustrating components of an example medical device programmer 14 (FIG. 1). Programmer 14 includes processor 80, memory 82, telemetry module 84, user interface 86, and power source 88. Processor 80 controls user interface 86 and telemetry module 84, and stores and retrieves information and instructions to and from memory 82. Programmer 14 may be configured for use as a clinician programmer or a patient programmer. Processor 80 may comprise any combination of one or more processors including one or more microprocessors, DSPs, ASICs, FPGAs, or other equivalent integrated or discrete logic circuitry. Accordingly, processor 80 may include any suitable structure, whether in hardware, software, firmware, or any combination thereof, to perform the functions ascribed herein to processor 80.

A user, such as a clinician or patient 12, may interact with programmer 14 through user interface 86. User interface 86 includes a display (not shown), such as a LCD or LED display or other type of screen, with which processor 80 may present information related to the therapy, a patient condition detected by programmer 14 or IMD 16 based on a frequency domain characteristic of a sensed bioelectrical signal, or electrical signals sensed via a plurality of sense electrode combinations. In addition, user interface 86 may include an input mechanism to receive input from the user. The input mechanisms may include, for example, buttons, a keypad (e.g., an alphanumeric keypad), a peripheral pointing device or another input mechanism that allows the user to navigate though user interfaces presented by processor 80 of programmer 14 and provide input.

If programmer 14 includes buttons and a keypad, the buttons may be dedicated to performing a certain function, i.e., a power button, or the buttons and the keypad may be soft keys that change function depending upon the section of the user interface currently viewed by the user. In addition, or instead, the screen (not shown) of programmer 14 may be a touch screen that allows the user to provide input directly to the user interface shown on the display. The user may use a stylus or their finger to provide input to the display. In other examples, user interface 86 also includes audio circuitry for providing audible notifications, instructions or other sounds to patient 12, receiving voice commands from patient 12, which may be useful if patient 12 has limited motor functions, or both. Patient 12, a clinician or another user may also interact with programmer 14 to manually select therapy programs, generate new therapy programs, modify therapy programs through individual or global adjustments, and transmit the new programs to IMD 16.

In some examples, at least some of the control of therapy delivery by IMD 16 may be implemented by processor 80 of programmer 14. For instance, in some examples, processor 80 may receive information representative of a bioelectrical signal of a patient. In this example, processor 60 of IMD 16 receives information representative of the bioelectrical signal and transmits such information to programmer 14.

Processor 80 may determine characteristics of two or more sensed frequency components of a plurality of sensed frequency components of the bioelectrical signal. Also, processor 80 may determine therapy parameters for two or more stimulation frequency components of a plurality of stimulation frequency components of a stimulation signal in response to determining the characteristics of the two or more sensed frequency components. In general, processor 80 may perform techniques similar to those described above with respect to processor 60 to determine the characteristics of two or more sensed frequency components and to determine therapy parameters for two or more stimulation frequency components.

In some examples, processor 80 may cause programmer 14 to output information indicative of the determined characteristics of the sensed frequency components. A user may input information of the therapy parameters for the stimulation frequency components. For example, programmer 14 may display the amplitude and/or phase of sensed frequency components. The user may then input amplitude and/or phase for the stimulation frequency components so that when IMD 16 delivers the stimulation signal, the symptoms of patient 12 may be addressed. Accordingly, in this example, processor 80 may receive information indicative of the therapy parameters in response to outputting the information indicative of the determined characteristics. Processor 80 may then determine the therapy parameters for the two or more stimulation frequency components based on the received information.

Processor 80 may cause stimulation generator 64 to deliver the stimulation signal. For example, processor 80 may output therapy parameters to IMD 16 and instruct IMD 16 as to when stimulation generator 64 is to deliver the stimulation signal. In some examples, processor 80 may cause programmer 14 to display the therapy parameters for user confirmation. The user may further modify the therapy parameters. In this example, processor 80 may cause stimulation generator 64 to deliver stimulation based on the modification to the determined therapy parameters.

Memory 82 may include instructions for operating user interface 86 and telemetry module 84, and for managing power source 88. In some examples, memory 82 may also store any therapy data retrieved from IMD 16 during the course of therapy, biomarker information, sensed bioelectrical brain signals, and the like. In some instances, the clinician may use this therapy data to determine the progression of the patient condition in order to plan future treatment for the movement disorder (or other patient condition) of patient 12. Memory 82 may include any volatile or nonvolatile memory, such as RAM, ROM, EEPROM or flash memory. Memory 82 may also include a removable memory portion that may be used to provide memory updates or increases in memory capacities. A removable memory may also allow sensitive patient data to be removed before programmer 14 is used by a different patient.

Wireless telemetry in programmer 14 may be accomplished by RF communication or proximal inductive interaction of external programmer 14 with IMD 16. This wireless communication is possible through the use of telemetry module 84. Accordingly, telemetry module 84 may be similar to the telemetry module contained within IMD 16. In other examples, programmer 14 may be capable of infrared communication or direct communication through a wired connection with other external devices. In this manner, other external devices may be capable of communicating with programmer 14 without needing to establish a secure wireless connection.

Power source 88 is configured to deliver operating power to the components of programmer 14. Power source 88 may include a battery and a power generation circuit to produce the operating power. In some examples, the battery may be rechargeable to allow extended operation. Recharging may be accomplished by electrically coupling power source 88 to a cradle or plug that is connected to an alternating current (AC) outlet. In addition, recharging may be accomplished through proximal inductive interaction between an external charger and an inductive charging coil within programmer 14. In other examples, traditional batteries (e.g., nickel cadmium or lithium ion batteries) may be used. In addition, programmer 14 may be directly coupled to an alternating current outlet to operate.

Figure 5:
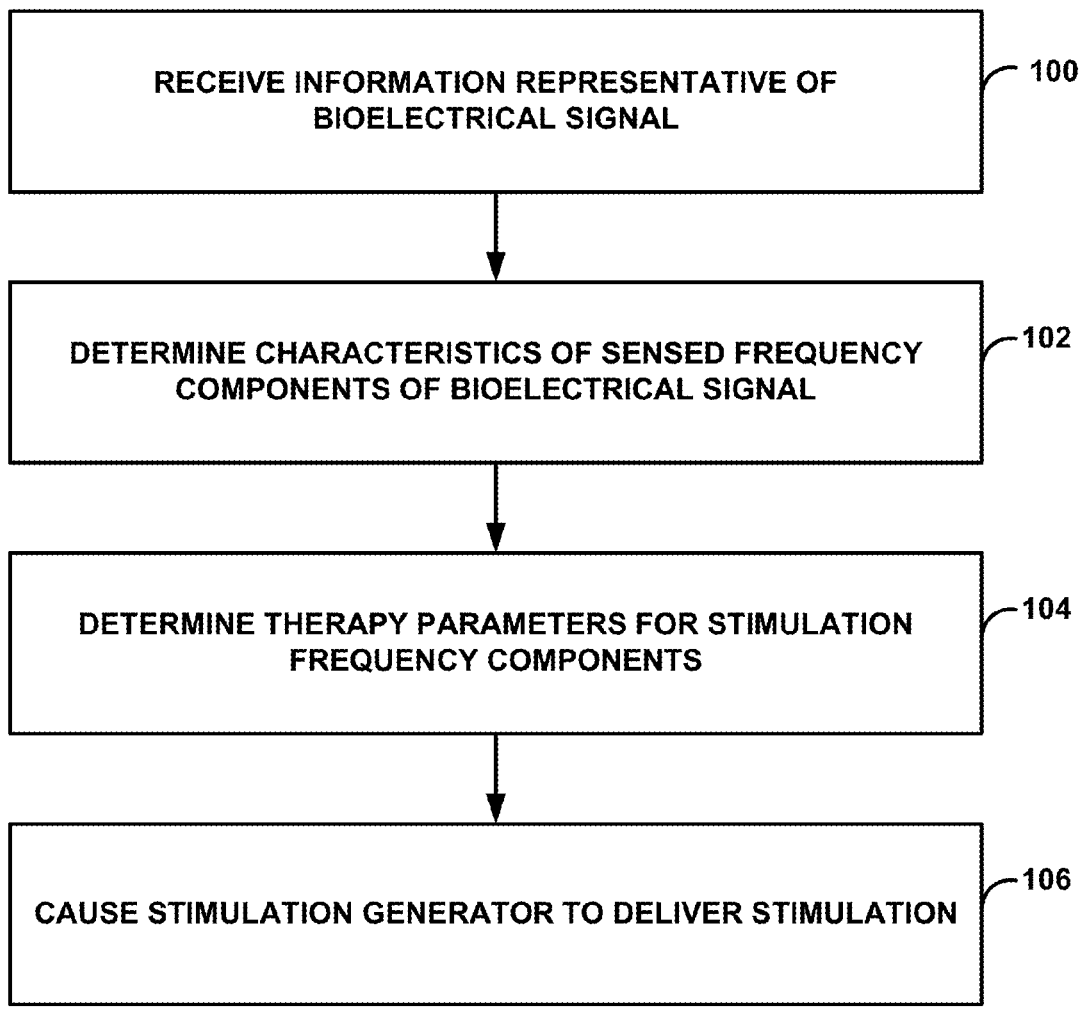
FIG. 5 is a flow diagram illustrating an example technique in accordance with one or more aspects of this disclosure.

FIG. 5 is a flow diagram illustrating an example technique in accordance with one or more aspects of this disclosure. In some examples, IMD 16 may perform the example techniques illustrated in FIG. 5. In some examples, programmer 14 may perform the example techniques described in FIG. 5. In some examples, a combination of IMD 16 and programmer 14 may perform the example techniques described in FIG. 5. For ease of description, FIG. 5 is described with respect to a device, examples of which include IMD 16 and programmer 14.

The device may be configured to receive information representative of a bioelectrical signal of patient 12 (e.g., IMD 16 may receive via electrodes 24, 26, or programmer 14 may receive from IMD 16, which receives from electrodes 24, 26) (100). The device may be configured to determine characteristics (e.g., amplitude and/or phase) of two or more sensed frequency components of a plurality of sensed frequency components, where the plurality of sensed frequency components together form the bioelectrical signal (102).

As described above, the device may be configured to determine therapy parameters (e.g., amplitude and/or phase) for two or more stimulation frequency components of a plurality of stimulation frequency components of a stimulation signal in response to determining the characteristics of the two or more sensed frequency components (104). Examples of the therapy parameters include one or more of amplitude, phase, and/or pulse width of two or more stimulation frequency components. For example, the device may determine an amplitude, phase, and/or pulse width for a first frequency component of the stimulation signal, and determine an amplitude, phase, and/or pulse width for a second frequency component of the stimulation signal. In some examples, one or more of the amplitude, phase, and/or pulse width of the first frequency component may be different than one or more of the amplitude, phase, and/or pulse width of the second frequency component.

In some examples, the device may automatically determine the therapy parameters of the stimulation signal based on the characteristics of the sensed frequency components. In some examples, the device may determine the therapy parameters of the stimulation signal based on feedback provided by a user for the therapy parameters of the stimulation frequency components. The device may cause stimulation generator 64 to deliver the stimulation signal (106).

In this manner, the device may adjust the stimulation signal based on the characteristics of the sensed frequency components of the bioelectrical signal. For example, the device may adjust one or more parameters, such as amplitude or phase, of the stimulation frequency components of the stimulation signal based on the frequency components of the bioelectrical signal. In some cases, the device may determine the amplitude and/or phase of a stimulation frequency component that corresponds to a sensed frequency component. For instance, based on the amplitude and/or phase of a sensed frequency component, the device may determine the amplitude and/or phase of a corresponding stimulation frequency component (e.g., so that the stimulation frequency component is additive with the natural frequency component in the bioelectrical signal generated in the patient's brain or subtract or disrupts the natural frequency component in the bioelectrical signal generated in the patient's brain). The corresponding stimulation frequency component may be at the same frequency as the sensed frequency component; however, this is not a requirement, and the stimulation frequency component may be at a different frequency than the sensed frequency component.

As described above, bioelectrical signals include a plurality of frequency components. In general, motor and cognitive, as well as other functions, are also associated with different oscillations (i.e., frequency components). In accordance with the techniques described in this disclosure, the therapy parameters for frequency components of the stimulation signal that are determined by IMD 16 or programmer 14 (e.g., determined based on the sensed frequency components or determined based on received information) may be weighted oscillations (e.g., the amplitude of the frequency components may be different), and the phase of the different oscillations (e.g., the phase of the frequency components) and pulse widths of the different oscillations (e.g., the pulse widths of the frequency components) may also be optimized for output.

Figure 6:
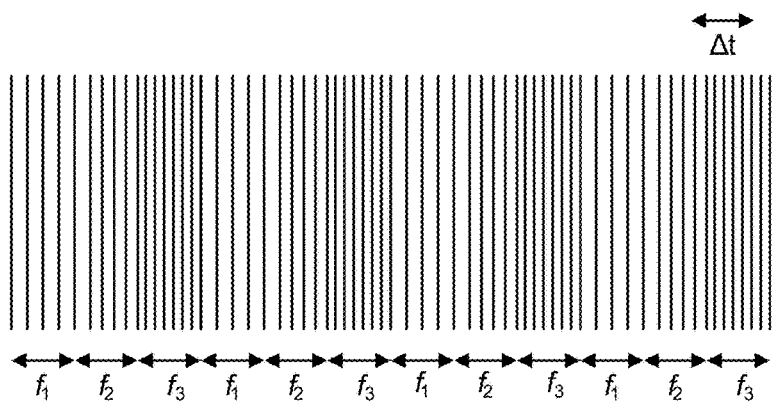
FIG. 6 is a conceptual diagram illustrating an example of a stimulation waveform.
Figure 7:
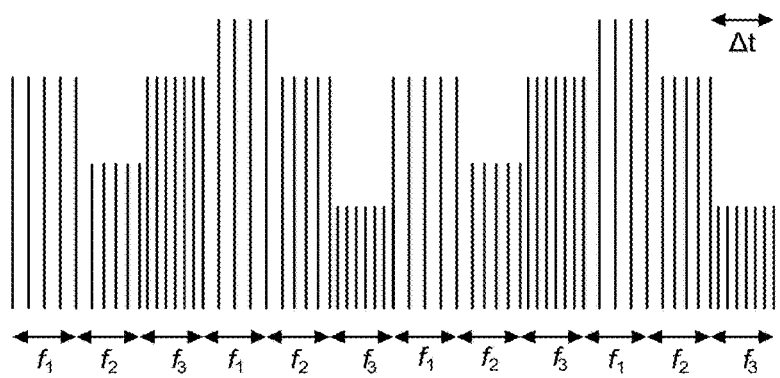
FIG. 7 is a conceptual diagram illustrating another example of a stimulation waveform.

FIGS. 6 and 7 are conceptual diagrams illustrating examples of stimulation waveform. For instance, FIGS. 6 and 7 illustrate an example in which there is sequential delivery of different frequency components. For example, IMD 16 or programmer 14 may have determined a single stimulation frequency component that is to be delivered for one period, followed by a different stimulation frequency component, and so forth. In other words, in FIGS. 6 and 7, the stimulation waveform first includes the frequency component $f_1$ for a given time of $\Delta t$, then the stimulation frequency changes to frequency component $f_2$ for a given time of $\Delta t$, and followed by frequency component $f_3$ for a given time of $\Delta t$. Then the pattern repeats. The time $\Delta t$ may be different for the different frequency components. In FIG. 7, both the amplitude and pulse width of the frequency components are modified so that the stimulation signal reaches or avoids certain neural populations.

Although the examples of FIGS. 6 and 7 may be considered as illustrating scenarios where the stimulation signal includes sequential transmission of different frequency components, the techniques described in this disclosure are not so limited. In some examples, the stimulation signal outputted by IMD 16 includes a plurality of frequency components that are being transmitted at the same time. Accordingly, this disclosure describes examples of a stimulation waveform that includes sequential transmission of different frequency components, or as an alternative an overlapping transmission of different frequency components, or as a further alternative a combination of the two (i.e., sequential transmission followed by overlapping transmission, or vice-versa).

In some examples, if two or more sensed frequency components are detected, a stimulation signal may be generated and delivered via one or more electrodes. For example, if the sensed frequencies are 5 Hz, 12 Hz, and 40 Hz, one electrode pair may be programmed to deliver a stimulation signal that has 5 Hz and 12 Hz frequency components and another electrode pair configured to deliver 40 Hz stimulation. In some examples, different electrode pairs may be configured to deliver stimulation signals with one or more of the sensed frequency components.

Figure 8:
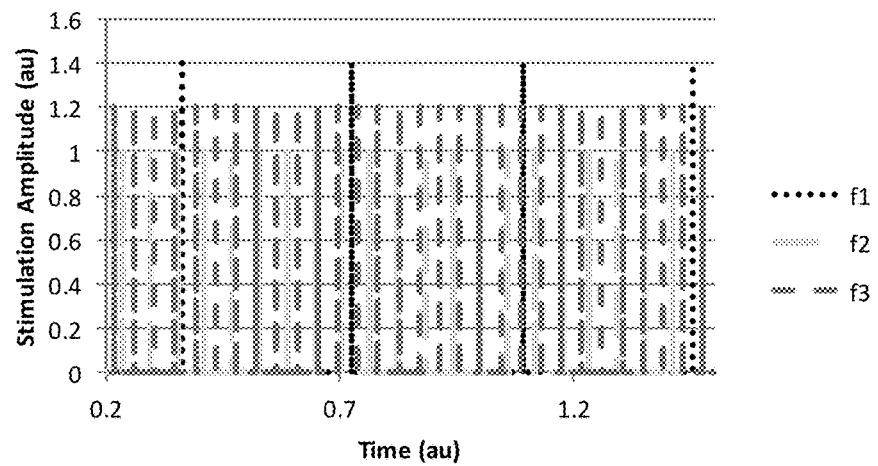
FIG. 8 is a graph illustrating another example of a stimulation waveform.

FIG. 8 is a conceptual diagram illustrating another example of a stimulation waveform. In the example illustrated in FIG. 8, IMD 16 outputs regular pulses of frequency components $f_1$, $f_2$, and $f_3$, each having different pulse widths. At times, however, IMD 16 delivers pulses of two or more of frequency components $f_1$, $f_2$, and $f_3$ at the same time. Also, as illustrated in FIG. 8, the amplitude of the frequency components $f_1$, $f_2$, and $f_3$ is different. Therefore, FIG. 8 illustrates an example with three stimulation frequency components having different amplitudes and phases that together from the stimulation signal delivered by IMD 16. The therapy parameters for the stimulation frequency components may be determined in response to the determining of characteristics of sensed frequency components. For instance, IMD 16 or programmer 14 may determine the therapy parameters for the stimulation frequency components based on the characteristics of the sensed frequency components. As another example, a user may provide information indicative of the therapy parameters, and IMD 16 or programmer 14 may determine the therapy parameters for the stimulation frequency components based on received information indicative of the therapy parameters.

While the techniques described above are primarily described as being performed by processor 60 of IMD 16 or processor 80 of programmer 14, in other examples, one or more other processors may perform any part of the techniques described herein alone or in addition to processor 60 or processor 80. Thus, reference to "a processor" may refer to "one or more processors." Likewise, "one or more processors" may refer to a single processor or multiple processors in different examples.

The techniques described in this disclosure, including those attributed to IMD 16, programmer 14, or various constituent components, may be implemented, at least in part, in hardware, software, firmware or any combination thereof. For example, various aspects of the techniques may be implemented within one or more processors, including one or more microprocessors, DSPs, ASICs, FPGAs, or any other equivalent integrated or discrete logic circuitry, as well as any combinations of such components, embodied in programmers, such as clinician or patient programmers, medical devices, or other devices.

In one or more examples, the functions described in this disclosure may be implemented in hardware, software, firmware, or any combination thereof. If implemented in software, the functions may be stored on, as one or more instructions or code, a computer-readable medium and executed by a hardware-based processing unit. Computer-readable media may include computer-readable storage media forming a tangible, non-transitory medium. Instructions may be executed by one or more processors, such as one or more DSPs, ASICs, FPGAs, general purpose microprocessors, or other equivalent integrated or discrete logic circuitry. Accordingly, the term "processor," as used herein may refer to one or more of any of the foregoing structure or any other structure suitable for implementation of the techniques described herein.

In addition, in some aspects, the functionality described herein may be provided within dedicated hardware and/or software modules. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components. Also, the techniques could be fully implemented in one or more circuits or logic elements. The techniques of this disclosure may be implemented in a wide variety of devices or apparatuses, including an IMD, an external programmer, a combination of an IMD and external programmer, an integrated circuit (IC) or a set of ICs, and/or discrete electrical circuitry, residing in an IMD and/or external programmer.

Various examples have been described. These and other examples are within the scope of the following claims.

What is claimed is:

1. A method comprising:
    receiving, with one or more processors, information representative of a bioelectrical signal of a patient;
    determining, in a frequency domain and with the one or more processors, one or more characteristics of two or more sensed frequency components of a plurality of sensed frequency components, wherein the plurality of sensed frequency components together forms the bioelectrical signal, wherein each sensed frequency component is a signal having a particular frequency, and wherein determining the one or more characteristics of the two or more sensed frequency components comprises determining phases of the two or more sensed frequency components;
    determining, in the frequency domain and with the one or more processors, therapy parameters for two or more stimulation frequency components of a plurality of stimulation frequency components of a stimulation signal in response to determining the characteristics of the two or more sensed frequency components, wherein each stimulation frequency component is a signal having a particular frequency, and wherein determining the therapy parameters comprises determining phases of the frequency components of the stimulation signal that are out of phase with the determined phases of the two or more sensed frequency components; and
    causing, with the one or more processors, a stimulation generator to deliver the stimulation signal.

2. The method of claim 1, wherein receiving information representative of the bioelectrical signal comprises receiving, with the one or more processors, the information representative of the bioelectrical signal from a sensing module configured to receive the bioelectrical signal sensed via one or more electrodes.

3. The method of claim 1, wherein determining the one or more characteristics of the two or more sensed frequency components comprises determining phases and amplitudes of the two or more sensed frequency components.

4. The method of claim 1, wherein determining the therapy parameters for the two or more stimulation frequency components comprises determining phases and amplitudes of the two or more stimulation frequency components.

5. The method of claim 1, further comprising:
    comparing the determined phases of the two or more sensed frequency components to one or more characteristics of a baseline signal of frequency components, wherein determining the therapy parameters for the two or more stimulation parameters comprises determining the phases for the two or more stimulation parameters based on the comparison.

6. The method of claim 1, further comprising:
    outputting information indicative of the determined therapy parameters; and
    receiving information for modification to the determined therapy parameters,
    wherein causing the stimulation generator to deliver the stimulation signal comprises causing the stimulation generator to deliver the stimulation signal based on the received information for modification to the determined therapy parameters.

7. The method of claim 1, wherein determining the therapy parameters comprises determining therapy parameters for two or more stimulation frequency components that correspond to the two or more sensed frequency components.

8. The method of claim 1, further comprising:
    outputting information indicative of the determined characteristics of the two or more sensed frequency components in response to determining the one or more characteristics of the two or more sensed frequency components; and receiving information indicative of the therapy parameters in response to outputting the information indicative of the determined one or more characteristics, wherein determining the therapy parameters comprises determining the therapy parameters for the two or more stimulation frequency components based on the received information.

9. The method of claim 1, further comprising:
determining that a patient state is an untreated state based on the one or more characteristics of the two or more sensed frequency components,
wherein determining therapy parameters comprises determining therapy parameters that are associated with a treated state for the patient state based on the determination that the patient state is the untreated state.

10. The method of claim 1, wherein determining therapy parameters further comprises determining a first pulse width for a first frequency component of the stimulation signal, and a second, different pulse width for a second, different frequency component of the stimulation signal.

11. A device comprising:
a processor configured to:
receive information representative of a bioelectrical signal of a patient;
determine, in a frequency domain, one or more characteristics of two or more sensed frequency components of a plurality of sensed frequency components, wherein the plurality of sensed frequency components together forms the bioelectrical signal, wherein each sensed frequency component is a signal having a particular frequency, and wherein to determine the one or more characteristics of the two or more sensed frequency components, the processor is configured to determine phases of the two or more sensed frequency components;
determine, in the frequency domain, therapy parameters for two or more stimulation frequency components of a plurality of stimulation frequency components of a stimulation signal in response to determining the one or more characteristics of the two or more sensed frequency components, wherein each stimulation frequency component is a signal having a particular frequency, and wherein to determine the therapy parameters, the processor is configured to determine phases of the frequency components of the stimulation signal that are out of phase with determined phases of the two or more sensed frequency components; and
cause a stimulation generator to deliver the stimulation signal; and
a memory configured to store the determined therapy parameters.

12. The device of claim 11, wherein the device comprises an implantable medical device (IMD), and wherein the IMD comprises the stimulation generator.

13. The device of claim 11, wherein the device comprises a programmer for an implantable medical device (IMD), and wherein the IMD comprises the stimulation generator.

14. The device of claim 11, wherein the processor is configured to receive the information representative of bioelectrical signal from a sensing module configured to receive the bioelectrical signal sensed via one or more electrodes.

15. The device of claim 11, wherein to determine the one or more characteristics of the two or more sensed frequency components, the processor is configured to determine phases and amplitudes of the two or more sensed frequency components.

16. The device of claim 11, wherein to determine the therapy parameters for the two or more stimulation frequency components, the processor is configured to determine phases and amplitudes of the two or more stimulation frequency components.

17. The device of claim 11, wherein the processor is configured to:
compare the determined phases of the two or more sensed frequency components to one or more characteristics of a baseline signal of frequency components,
wherein to determine the therapy parameters for the two or more stimulation parameters, the processor is configured to determine the phases for the two or more stimulation parameters based on the comparison.

18. The device of claim 11, wherein the processor is configured to:
output information indicative of the determined therapy parameters; and
receive information for modification to the determined therapy parameters,
wherein to cause the stimulation generator to deliver the stimulation signal, the processor is configured to cause the stimulation generator to deliver the stimulation signal based on the received information for modification to the determined therapy parameters.

19. The device of claim 11, wherein to determine the therapy parameters, the processor is configured to determine therapy parameters for two or more stimulation frequency components that correspond to the two or more sensed frequency components.

20. The device of claim 11, wherein the processor is configured to:
output information indicative of the determined one or more characteristics of the two or more sensed frequency components in response to determining the one or more characteristics of the two or more sensed frequency components; and
receive information indicative of the therapy parameters in response to outputting the information indicative of the determined one or more characteristics,
wherein to determine the therapy parameters, the processor is configured to determine the therapy parameters for the two or more stimulation frequency components based on the received information.

21. The device of claim 11, wherein the processor is configured to determine that a patient state is an untreated state based on the one or more characteristics of the two or more sensed frequency components, and wherein to determine therapy parameters, the processor is configured to determine therapy parameters that are associated with a treated state for the patient state based on the determination that the patient state is the untreated state.

22. The device of claim 11, wherein to determine therapy parameters, the processor is further configured to determine a first pulse width for a first frequency component of the stimulation signal, and a second, different pulse width for a second, different frequency component of the stimulation signal.

23. A non-transitory computer-readable storage medium having instructions stored thereon that when executed cause one or more processors to:
receive information representative of a bioelectrical signal of a patient;
determine, in a frequency domain, one or more characteristics of two or more sensed frequency components of a plurality of sensed frequency components, wherein the plurality of sensed frequency components together forms the bioelectrical signal, wherein each sensed frequency component is a signal having a particular frequency, and wherein the instructions that cause the one or more processors to determine the one or more characteristics of the two or more sensed frequency components comprise instructions that cause the one or more processors to determine phases of the two or more sensed frequency components;

determine, in the frequency domain, therapy parameters for two or more stimulation frequency components of a plurality of stimulation frequency components of a stimulation signal in response to determining the one or more characteristics of the two or more sensed frequency components, wherein each stimulation frequency component is a signal having a particular frequency, and wherein the instructions that cause the one or more processors to determine the therapy parameters comprise instructions that cause the one or more processors to determine phases of the frequency components of the stimulation signal that are out of phase with determined phases of the two or more sensed frequency components; and cause a stimulation generator to deliver the stimulation signal.

24. The non-transitory computer-readable storage medium of claim 23, wherein the instructions that cause the one or more processors to determine the one or more characteristics of the two or more sensed frequency components comprise instructions that cause the one or more processors to determine phases and amplitudes of the two or more sensed frequency components.

25. The non-transitory computer-readable storage medium of claim 23, wherein the instructions that cause the one or more processors to determine the therapy parameters for the two or more stimulation frequency components comprise instructions that cause the one or more processors to determine phases, amplitudes, and pulse widths of the two or more stimulation frequency components.

26. A device comprising:
means for receiving information representative of a bioelectrical signal of a patient;
means for determining, in a frequency domain, one or more characteristics of two or more sensed frequency components of a plurality of sensed frequency components, wherein the plurality of sensed frequency components together forms the bioelectrical signal, wherein each sensed frequency component is a signal having a particular frequency, and wherein the means for determining the one or more characteristics of the two or more sensed frequency components comprises means for determining phases of the two or more sensed frequency components;
means for determining, in the frequency domain, therapy parameters for two or more stimulation frequency components of a plurality of stimulation frequency components of a stimulation signal in response to determining the one or more characteristics of the two or more sensed frequency components, wherein each stimulation frequency component is a signal having a particular frequency, and wherein the means determining the therapy parameters comprises means for determining phases of the frequency components of the stimulation signal that are out of phase with the determined phases of the two or more sensed frequency components; and
means for causing a stimulation generator to deliver the stimulation signal.

27. The device of claim 26, wherein the means for determining the one or more characteristics of the two or more sensed frequency components comprises means for determining phases and amplitudes of the two or more sensed frequency components.

28. The device of claim 26, wherein the means for determining the therapy parameters for the two or more stimulation frequency components comprises means for determining phases, amplitudes, and pulse widths of the two or more stimulation frequency components.

* * * * *